United States Patent [19]

Altshuler et al.

[11] Patent Number: 4,481,946
[45] Date of Patent: Nov. 13, 1984

[54] BONE MARROW TRANSPLANT METHOD AND APPARATUS

[76] Inventors: John H. Altshuler, 5700 Dunbarton Dr., Englewood, Colo. 80110; Dean T. Farrish, 6620 Trailway Cir., Parker, Colo. 80134

[21] Appl. No.: 177,875

[22] Filed: Aug. 14, 1980

[51] Int. Cl.$^3$ ............................................. A61M 5/00
[52] U.S. Cl. ........................................ 604/4; 604/28; 604/44
[58] Field of Search .......... 128/214 R, 214 B, 214 D, 128/214 F, 214.2, DIG. 12, 274, 213, 234, 237; 604/4, 27, 28, 43, 44

[56] References Cited

U.S. PATENT DOCUMENTS

| | | | |
|---|---|---|---|
| 2,496,559 | 2/1950 | Piechaczek | 128/214 B |
| 3,489,145 | 1/1970 | Judson et al. | 128/214 R |
| 3,808,432 | 4/1974 | Djerassi | 128/214 R |

Primary Examiner—Stephen C. Pellegrino

[57] ABSTRACT

A bone marrow method and apparatus as been devised for the efficient recovery of bone marrow from a donor or patient by inserting a pair of aspiration needles at the intended site of removal and, through connection with a pair of syringes, the pressure is regulated to bring about selective removal of bone marrow and sinusoidal blood through one of the aspiration needles while positively forcing an intravenous solution through the other of the aspiration needles to replace the bone marrow removed from the site. The bone marrow and sinusoidal blood are drawn into a chamber for mixture with another intravenous solution and thereafter forced into a collection bag. A disposable assembly is provided for ready interchangeable use in association with a fluid flow and valve control unit in carrying out the method and principles of the present invention.

13 Claims, 9 Drawing Figures

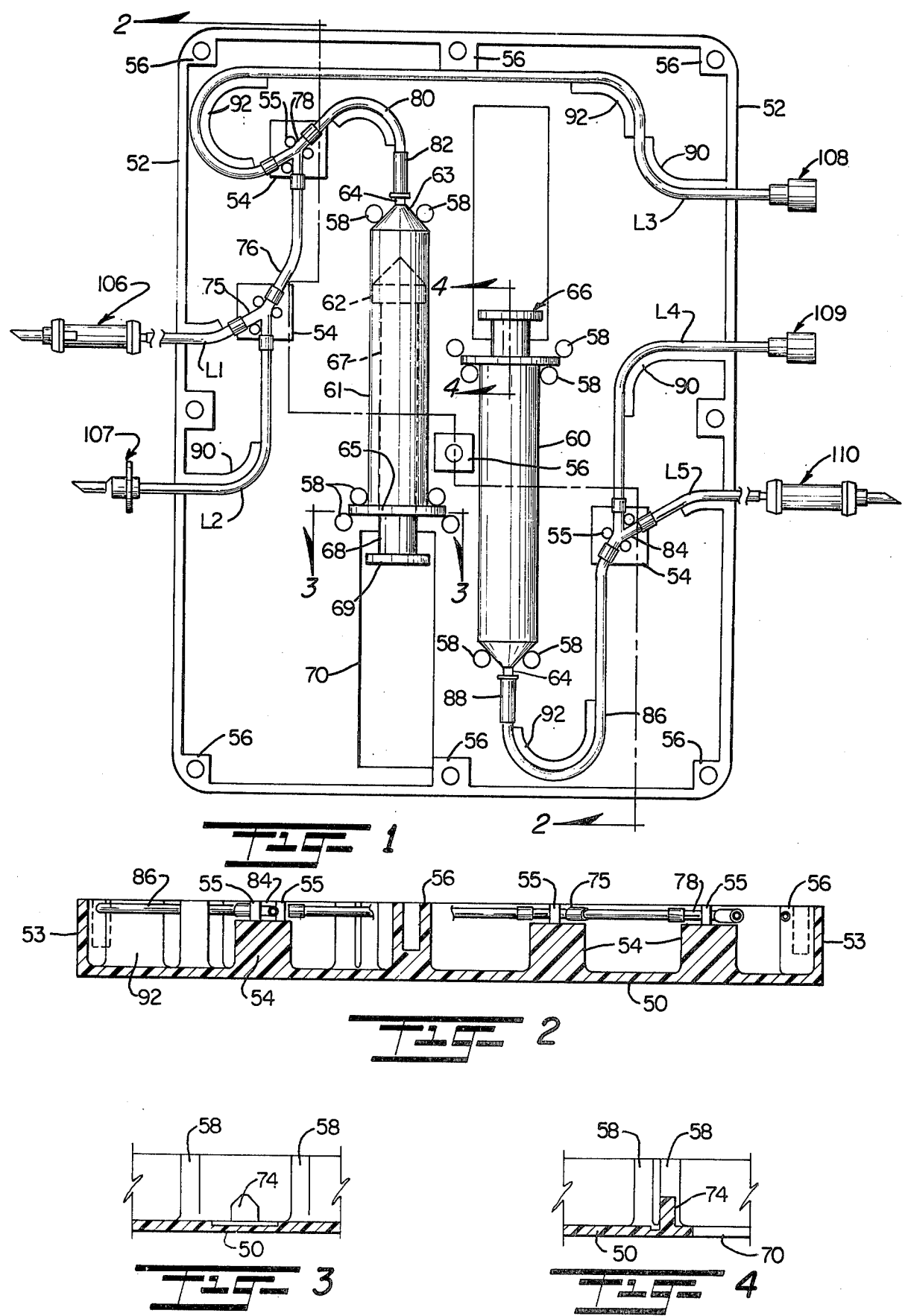

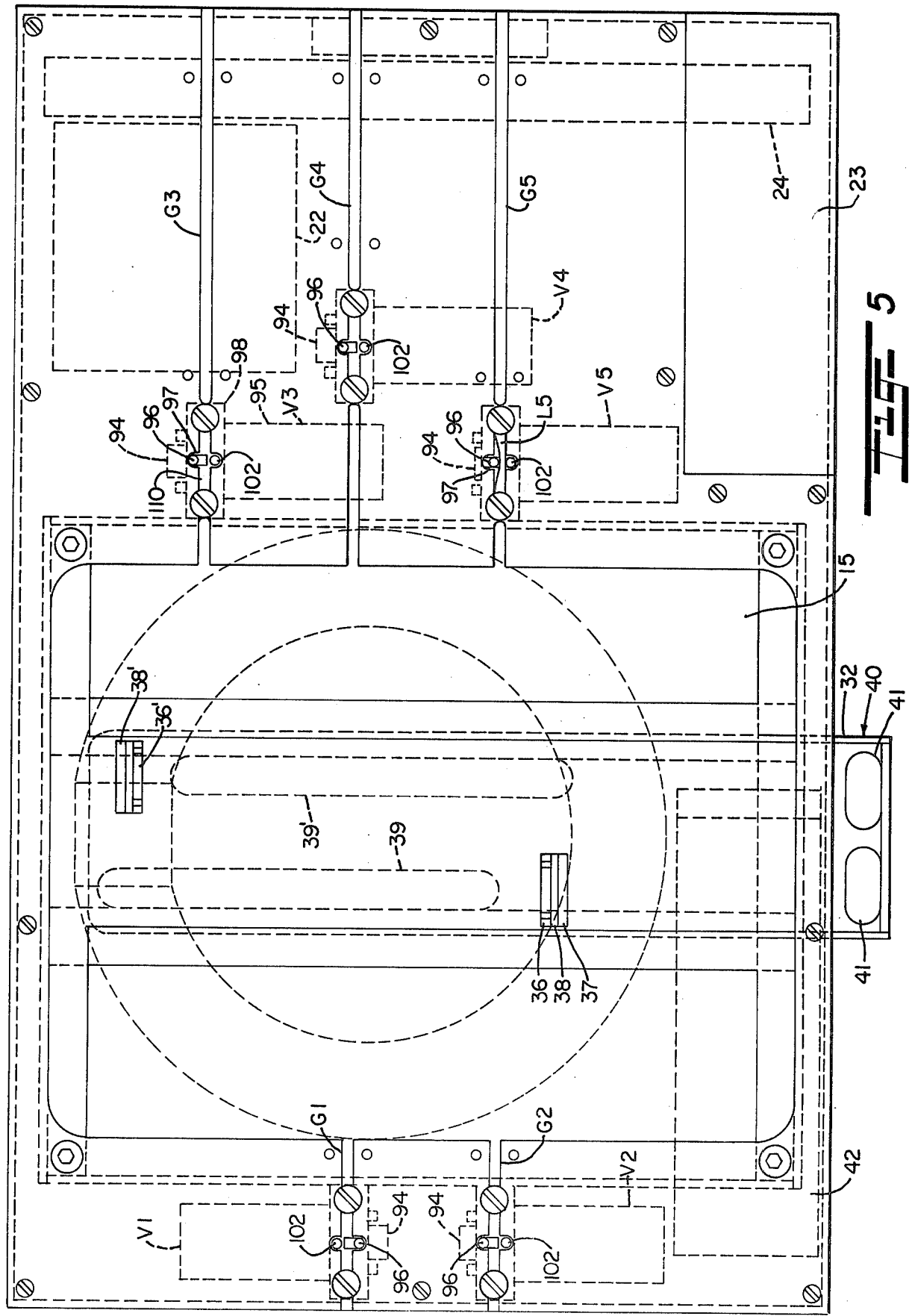

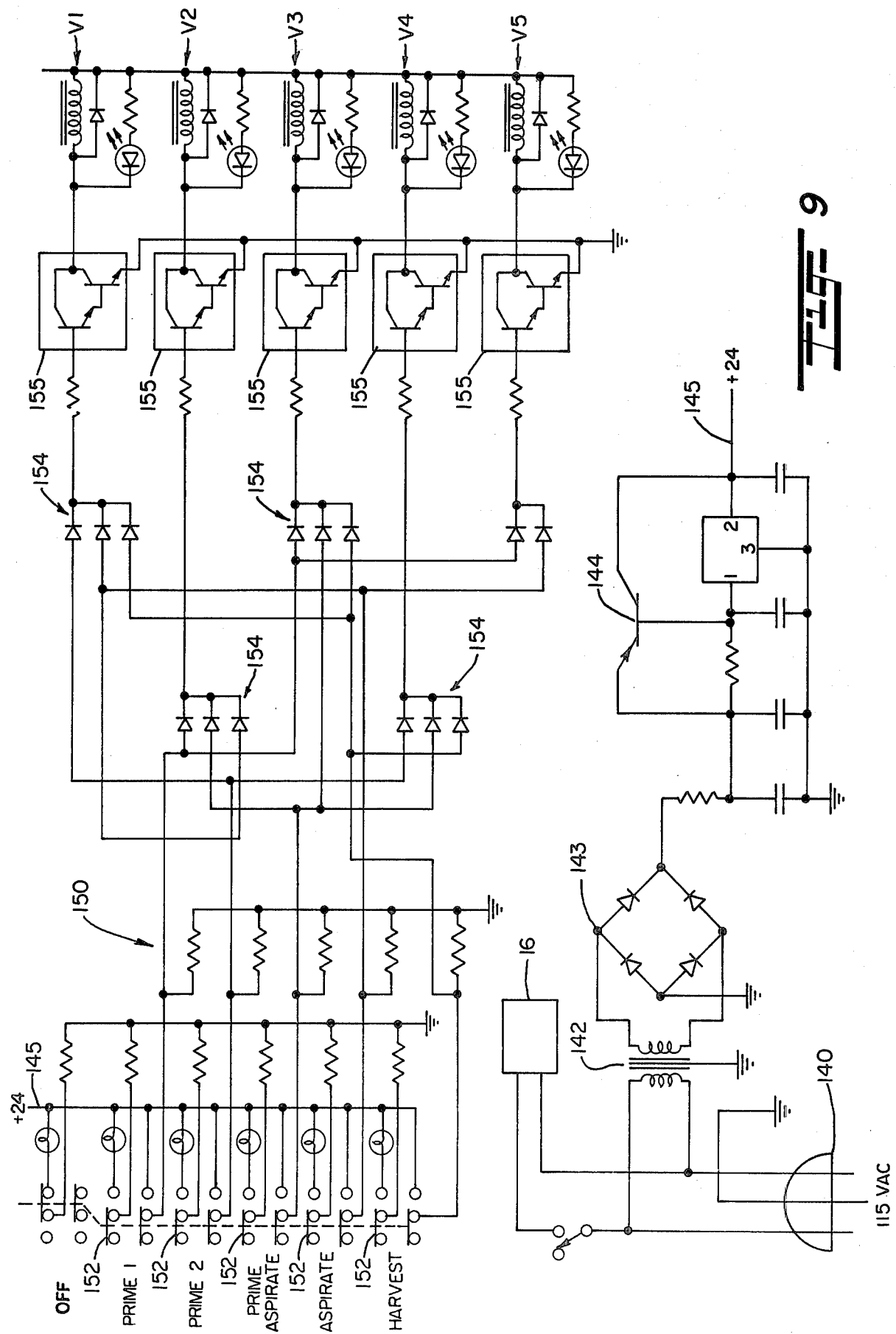

BONE MARROW TRANSPLANT METHOD AND APPARATUS

This invention relates to a novel and improved method and apparatus adaptable for use in medical transplant procedures; and more particularly to a method and apparatus for efficiently recovering bone marrow in bone marrow transplant operations.

BACKGROUND AND FIELD OF THE INVENTION

In the past, bone marrow transplants have been performed with success but have involved considerable pain due mainly to the number of bone marrow aspirations which must be performed. Bone marrow is comprised of bone marrow cells and large volumes of sinusoidal blood. For instance, it is not uncommon to have to insert a needle on the order of fifteen to seventy times into different sites or locations in order to recover acceptable quantities of bone marrow. Moreover, the bone marrow which is extracted is not separated from the sinusoidal blood, and in transfusing substantial volumes of material into the recipient, the bone marrow cavity is so finite and limited in capacity that it cannot readily accommodate huge volumes of blood and bone marrow. Thus, it is customary to inject the mass of material into the vein and depend upon the bone marrow present to find its way back into the marrow of the patient so as to function as normal marrow and undergo normal growth. A typical case requiring bone marrow transplantation is one in which healthy bone marrow is removed from a cancer patient prior to chemotherapy and the same bone marrow reinfused into the patient after chemotherapy. Another example is the need for bone marrow transplantation into a patient with decreased bone marrow function as in aplastic anemia or bone marrow failure due to drugs. In this latter situation, healthy bone marrow must be removed from a healthy donor with the healthy marrow being infused into the recipient patient.

It is therefore desirable to provide for a method and apparatus by means of which bone marrow may be harvested from a patient with a minimal number of needle placements which is capable of being performed under local anethesia over a relatively short period of time. Moreover, it is desirable that the procedure be virtually painless once the needles are inserted into the patient so as to avoid activation of stretch receptors in the marrow cavity.

SUMMARY OF THE INVENTION

It is therefore an object of the present invention to provide for a novel and improved method and apparatus for bone marrow transplants.

It is another object of the present invention to provide for a novel and improved method of carrying out bone marrow transplant operations in which the bone marrow can be withdrawn from a single site and collected for injection into a patient and in such way as to eliminate stretching or activation of the nerve stretch receptors in the marrow cavity thereby virtually eliminating bone marrow aspiration pain.

A further object of the present invention is to provide for a novel and improved bone marrow transplant apparatus including common actuating means to regulate the relative pressures in the various lines leading to and from a donor or patient.

It is an additional object of the present invention to provide in a bone marrow apparatus for a disposable assembly removably connectable to the patient as well as to various sources of solution supply and collector for the purpose of carrying out bone marrow transplant procedures in a safe, rapid and relatively painless manner.

In accordance with the present invention, a preferred form of bone marrow apparatus is capable of effecting removal of bone marrow and sinusoidal blood from a donor or patient at a single site, the material withdrawn from the patient being replaced by a suitable form of intravenous solution, such as, a mixture of an anticoagulant and saline or electrolyte solution. The bone marrow and sinusoidal blood removed from the patient are transferred either into a cell separator or suitable collection bag so as to permit separation of the bone marrow for subsequent processing or reinjection back into the same patient or into another patient. In the removal of the bone marrow from the patient or donor, an intravenous solution consisting of heparin or other anticoagulant compositions together with a saline solution are mixed with the bone marrow and sinusoidal blood preliminary to transfer into the separating or collecting means.

These steps ae accomplished in the present invention by a unique form of apparatus in which a series of lines ae directed from a chamber section to a source of intravenous solution, an aspiration needle, a second source of intravenous solution and a suitable separating or collection source as described. The chamber section is characterized by being capable of simultaneously applying negative pressure to the solution lines leading from the intravenous solution sources in order to prime the lines and to purge them of any air. The solution lines are then closed and a positive pressure applied to redirect the intravenous solution into the donor while negative pressure is applied to withdraw the bone marrow material into a chamber for admixture with the intravenous solution, following which a positive pressure is applied to transfer the mixture of the intravenous solution and bone marrow material into the separating or collection source. A single chamber with a double-acting plunger may be employed in one form to carry out the steps of the present invention, but in the preferred form a dual chamber having separate plungers are arranged to be simultaneously controllable by a common actuator to establish the desired positive and negative pressures in the respective lines.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a top plan view of a preferred form of disposable assembly adaptable for use in carrying out bone marrow transplant procedures in accordance with the present invention;

FIG. 2 is a cross-sectional view taken about lines 2—2 of FIG. 1;

FIG. 3 is a cross-sectional view taken about lines 3—3 of FIG. 1;

FIG. 4 is a cross-sectional view taken about lines 4—4 of FIG. 1;

FIG. 5 is a plan view of a preferred form of cabinet and control system used in association with the disposable assembly shown in FIG. 1;

FIG. 9 is a schematic view of one form of electrical control system for the apparatus of the present invention.

DETAILED DESCRIPTION OF THE PREFERRED EMBODIMENT

Figure 6:
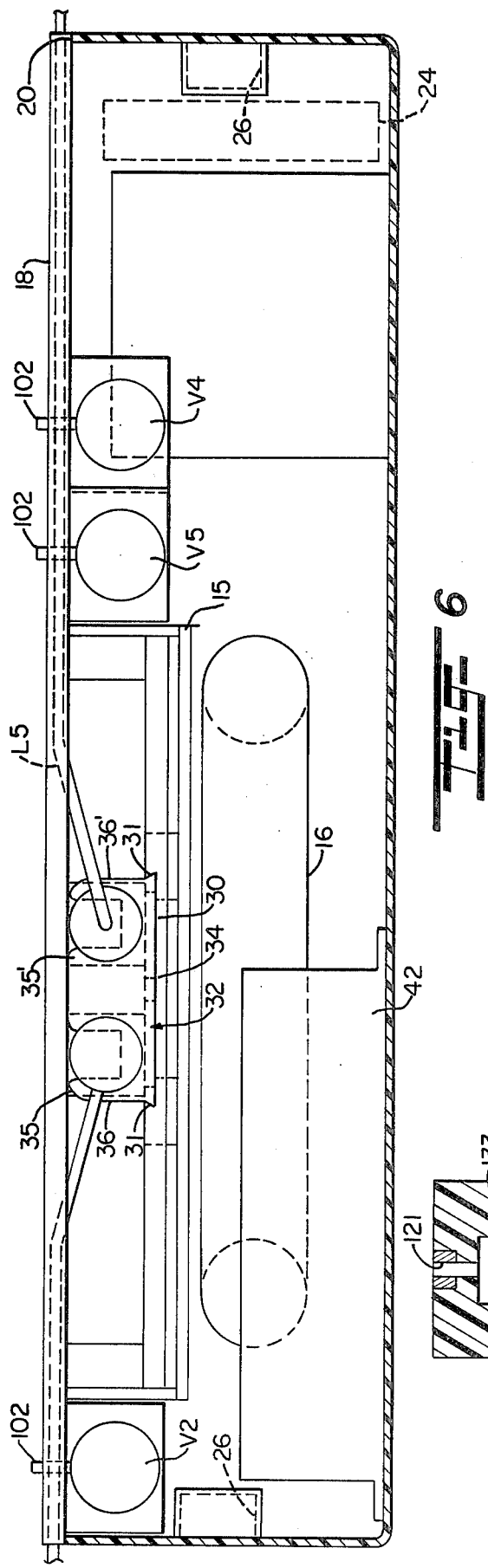
FIG. 6 is an end view of the cabinet shown in FIG. 5.

Referring to FIGS. 5 and 6, a cabinet or base 10 is provided for mounting of a disposable assembly 12, the latter being illustrated in FIGS. 1 to 4. The cabinet 10 is broadly comprised of a relatively shallow, generally rectangular receptacle 14 preferably comprised of a transparent bottom panel 15 with a generally circular light tube or lamp 16 mounted beneath the panel.

To one side of the receptacle are a pair of solenoid-operated control valves designated at $V_1$ and $V_2$; and to the opposite side of the receptacle are solenoid-operated control valves $V_3$, $V_4$ and $V_5$. Each control valve is mounted in association with an elongated groove designated $G_1$ to $G_5$, respectively, and each groove extending from communication with a sidewall of the receptacle and extending in a longitudinal direction across the top surface 18 of a cover plate designated at 20 which is removably secured over the cabinet by means of suitable fasteners 21. In addition, the cabinet is designed to contain the necessary power source and controls for operation of the solenoids including transformer section 22, control panel 23 and circuit board section 24. Opposite end walls of the cabinet are provided with shallow recessed areas 26 which facilitate grasping of the unit or in other words serve as hand grips.

From a consideration of FIGS. 5 and 6, it will be noted that the lower panel 15 of the receptacle is provided with a shallow groove 30 which extends intermediately across the length of the receptacle and in a direction transversely to the length of the entire cabinet. The groove is provided with dovetailed sides 31 to permit retention and slidable insertion of an actuator assembly 32, the actuator including a lower flat plate 34 of oblong configuration adapted to traverse the entire length of the groove 30 and having upstanding, plunger-engaging brackets 35 and 35'. The bracket 35 is located just less than halfway along the length of the slide 34, and the bracket 35' is located in offset relation to bracket 35 and at a position adjacent to the distal end of the slide 34. Each bracket comprises closely-spaced parallel wall sections including a generally channel-shaped wall section 36 and 36', respectively, and a solid wall section 37 and 37', respectively, with a narrow recess 38 and 38', respectively, formed between the wall sections, all for a purpose to be described. In addition, each bracket is aligned with a slot 39 and 39', respectively, each slot being of narrow elongated configuration and being formed through the thickness of the slide member in longitudinally centered relation to the bracket to serve as a seating portion for a syringe to be hereinafter described and to permit back lighting of the syringe body. In addition, the slide has a forwardly projecting hand grip 40 at one end projecting from the sidewall of the receptacle with finger openings 41 to facilitate grasping and hand actuation or slidable movement of the entire actuator assembly 32. Located immediately below the receptacle portion of the cabinet is a relatively large cavity 42 for placement of ballast in the operation of lamp 16.

FIGS. 1 to 4 illustrate the preferred form of disposable, fluid flow control assembly 12 which is broadly comprised of a relatively shallow tray having a bottom panel 50, side panels 52 and upstanding end panels 53. Generally, the tray 12 is sized to be insertable into the receptacle 14 with the end panels 53 aligned with opposite ends of the receptacle and with the upper surface of the tray flush with the upper surface of the receptacle. Upstanding locator blocks designated at 54 are provided at spaced locations within the tray, each having a series of three upstanding locator pins 55 to serve as a means of location and support for fluid flow delivery lines to be described. Bosses 56 are positioned at spaced intervals around the periphery of the tray and at the center of the tray to threadedly receive the fastener screws 21 which extend through aligned bores in cover plate 20 of the cabinet. Also, locator pins 58 project upwardly from the bottom panel 50 of the tray to facilitate the location and mounting of a pair of chambers or syringes 60 and 61 in horizontally extending, parallel but oppositely facing relation in a direction lengthwise of the tray and at a location aligned over the hand actuator assembly 32 in the receptacle. Each syringe may be of conventional construction and for example may be a Becton-Dickinson "Monoject" 20 cc. syringe having a outer elongated cylindrical chamber section 62 terminating in a forward tapered end 63 which merges into a tube 64, and a flange 65 is disposed at its opposite end. A plunger 66 is mounted for slidable movement through each chamber section 62 and suitably provided with a piston head 67, a generally elongated shank 68 of X-shaped cross-section and handle or flange 69 at its external or trailing end. Each chamber section 62 of a syringe is seated in the tray such that the tapered end abuts a pair of spaced locator pins 58 and the flange 65 is snugly positioned between spaced pairs of locator pins 58 as illustrated. Immediately behind the locator pins 58 for the flange 65 is an elongated cavity 70 which extends through the thickness of the bottom panel 50 of the tray in alignment with the upstanding brackets 35 and 35', respectively, of the hand actuator assembly 32. The flanged end 69 of each plunger 66 is inserted into the groove 38 or 38' of a respective bracket with the channel-shaped wall section 36 or 36' flanking opposite sides of the plunger portion 68 and the solid wall portion of the bracket 38 or 38' located on the external side of the flanged end 69. Thus in the relationship shown in FIG. 5, the syringe 60 would have its plunger 66 extended to a position such that the flanged end 69 would be aligned with the bracket 35' in the position illustrated in FIG. 5 while the syringe 61 would have its flanged end 69 in the retracted position for alignment with the bracket 35. In response to sliding movement of the hand actuator assembly 32 outwardly, i.e., in a direction advancing downwardly as viewed in FIG. 5, the plunger 66 for syringe 61 is extended in following the movement of bracket 35 while the plunger 66 for syringe 61 is retracted. In other words, negative pressure would be created ahead of the plunger 66 in the syringe 61 while positive pressure would be applied or created ahead of the plunger in the syringe 60 to force fluid in that chamber through the tube 64.

As best seen from a consideration of FIGS. 3 and 4, the generally web-shaped or X-shaped cross-section of the plunger portions 68 are each supported on a generally V-shaped pin 74 which projects upwardly from the tray 50 adjacent to and at one end of each of the cavities 70. The support pins 74 operate to prevent accidental rotation of the plunger elements 66 as they are extended and retracted with respect to their chambers 62.

A series of delivery lines in the form of flexible conduits, such as, plastic tubing extend from the chambers 60 and 61 in such a manner as to be aligned with the grooves $G_1$ to $G_5$, as previously described with reference to FIGS. 5 and 6, and the external ends of the delivery lines which are directed away from opposite side panels 52 of the tray are designated $L_1$ to $L_5$, respectively. It will be noted that delivery lines $L_1$ and $L_2$ are joined at a tubular Y junction 75 to a common line 76 which in turn is joined at a Y junction 78 to delivery line $L_3$. Each of the Y junctions 75 and 78 are supported on a block 54 between the locator pins 55 and the common line 76 from lines $L_1$ and $L_2$ together with the line $L_3$ is joined to the Y junction 78 to line 80 which is connected by a suitable fitting or sleeve 82 to the tube 64 of chamber 61. Delivery lines $L_4$ and $L_5$ are joined through Y junction 84 to common line 86 which is secured by a fitting 88 to the tube 64 of the chamber 60. Proper alignment of the delivery lines $L_1$ to $L_5$ in relation to the respective grooves $G_1$ to $G_5$ on the upper surface of the cabinet is established by a plurality of locator ribs 90 which are located at spaced intervals around the periphery of the tray. Intermediate ribs 92 project upwardly from the bottom panel 52 of the tray to assist in guiding the delivery lines between the tubes 64 and periphery of the tray. When the fluid flow control assembly 12 is positioned in the receptacle 15, as illustrated in FIG. 5, the delivery lines $L_1$ and $L_2$ are aligned with the grooves $G_1$ and $G_2$, respectively along one side of the receptacle. Delivery lines $L_3$ to $L_5$ are aligned with grooves $G_3$ to $G_5$, respectively on the opposite side of the receptacle.

Referring to FIG. 5, it will be noted that a solenoid-operated control valve V is positioned beneath each of the grooves G, the valves being designated $V_1$ to $V_5$ for each of the respective grooves $G_1$ to $G_5$ and associated delivery lines $L_1$ to $L_5$. Specifically, the delivery lines L are positioned in the manner shown in FIG. 6 such that they are fully inserted into their respective grooves G and are held in position by the cover plate 20. Each of the solenoid control valves V is correspondingly made up of a plunger or armature 94 which projects horizontally from one end of a solenoid 95, and each plunger 94 carries a movable valve element in the form of a pin 96 which projects upwardly from the plunger through a transverse slot 97 in the cover plate 20 at the leading end of each solenoid 95, there being a slot 97 which intersects each one of the grooves $G_1$ to $G_5$. A mounting block 98 is mounted with its upper surface 100 directly beneath one of the associated grooves $G_1$ to $G_5$ with the movable pin 96 and a stationary upwardly projecting pin 102 on the mounting block inserted in the slot 97 on opposite sides of the groove G. When the solenoid is de-energized, the plunger will normally be extended, as illustrated at valve location $V_3$ with the movable pin 96 flanking one side of the groove G and the stationary pin 102 flanking the opposite side. When the solenoid is energized, it will cause retraction of the plunger and sliding movement of the pin 96 through the slot 97 into engagement with the delivery line L disposed in the groove G so as to pinch off or close the line as illustrated at solenoid $V_5$. Accordingly, each solenoid is independently controllable to open or close its associated delivery line in regulating the flow of material through that line.

In carrying out bone marrow transplant operations, in accordance with the present invention, the delivery line $L_1$ extends from the associated groove $G_1$ for connection to an intravenous drip chamber designated at 106. Line $L_2$ extends from groove $G_2$ for connection to a collection bag 107, such as, a collection bag manufactured and sold by Travenol Labs of Deerfield, Ill., under Code No. 4R6308. Line $L_3$ extends from its groove $G_3$ for connection to a Luer Lock fitting 108. Similarly, line $L_4$ is connected to a Luer Lock fitting 109, and finally line $L_5$ is connected to a second intravenous drip chamber 110. In a well-known manner, the Luer Lock fittings facilitate releasable connection of aspiration and infusion needles placed in the patient. Preferably, the intravenous drip chamber 106 contains a saline or electrolyte solution having a predetermined concentration of heparin on the order of 4 units heparin per cubic centimeter for mixture with bone marrow and sinusoidal blood recovered from the patient through line $L_3$. Similarly, the drip chamber 110 contains a saline or electrolyte solution with predetermined concentrations of heparin, on the order of 4 units/cc. which is injected into the patient through line 109. In carrying out a bone marrow transplant, the various delivery lines should be primed or purged of any air so as to be completely filled with fluid as a preliminary to recovery or removal of bone marrow. Referring to the control panel and control buttons shown in FIG. 8, this is carried out by depressing "PRIME 1" to open valves $V_1$ and $V_4$ and close valves $V_2$, $V_3$, and $V_5$, then depressing "PRIME 2" to reverse the position of the valves to open $V_2$, $V_3$ and $V_5$ while closing $V_1$ and $V_4$, at the same time operating the hand actuator assembly 32 until the tubes are filled with the intravenous solution from drip chamber 106, the procedure being repeated until no bubbles appear in any of the lines. As a next step, "CLAMP" is depressed so that valves $V_1$ and $V_5$ are open and valves $V_2$, $V_3$ and $V_4$ are closed so as to hold all output lines closed to eliminate leakage as a preliminary to insertion of the aspiration and infusion needles into the patient in the "CLAMP" position. Prior to attaching the Luer Locks 108 and 109 to the aspiration and infusion bone marrow needles, the bone marrow cavity is anti-coagulated with 2000 units of heparin. The needles connected to the Luer Locks 108 and 109 specifically are inserted into the same bone marrow site, such as as the iliac crest. As a next step, "PRIME ASPIRATE" is depressed to open the valves $V_1$ and $V_5$ open and close the remaining valves, then the hand actuator 32 is pulled out or withdrawn partially to permit the entry of the intravenous solution from drip chamber 106 prior to aspiration. At this point, "ASPIRATE" is depressed so that valves $V_3$ and $V_4$ are opened and valves $V_1$, $V_2$, and $V_5$ are closed followed by fully withdrawing the hand actuator assembly in order to extract marrow from the patient. This is brought about by reason of the negative pressure created in the chamber 61 to induce the flow of bone marrow and sinusoidal blood into chamber 61. After the chamber 61 has been filled, "HARVEST" is depressed to open valves $V_2$ and $V_5$ and close valves $V_1$, $V_3$ and $V_4$, following which the hand actuator is pushed in so as to retract the plunger 66 through chamber 61 and force the mixture of bone marrow, sinusoidal blood and intravenous solution through the line L₂ which is connected to the collection bag spike 107.

Figure 8:
FIG. 8 is a cross-sectional view of a modified form of double-acting syringe which may be employed in the present invention.

A modified form of chamber arrangement is shown in FIG. 8 which is adaptable for use in place of the double syringe assemblies 60, 61 of the preferred form. Specifically referring to FIG. 8, an outer cylinder 120 includes a first port 121 at its leading end and a second port 122 in the sidewall adjacent to its rearward end. An O-ring seal 124 is positioned at the rearward end across the end surface of a closure 126 which is threadedly connected to the rear end of the cylinder 120. A central bore 127 in the closure permits close-fitting slidable insertion of a plunger rod 128. Plunger rod 128 has an external handle 130 and a piston head 131 which is arranged for slidable movement through the cylinder 120 in close-fitting sealed relation to its inner wall so as to in effect divide the inner space of the cylinder into a forward chamber 133 and a rear chamber 134. In this fashion, the forward chamber 133 is in communication with the end port 121 and the rearward chamber 134 is in communication with the rearward sidewall port 122. Reference is now made to FIG. 1 for an understanding of the manner in which the delivery lines would be connectable to the single, double-acting syringe: The delivery line 80 is connectable to the port 121 while the delivery line 86 is connectable to the sidewall port 122. Assuming that the double-acting syringe 120 is merely held in the hand, it will be appreciated that the system may be primed by successively opening and closing the same series of valves as described in connection with the preferred form as the plunger 128 is worked back and forth through the cylinder until the delivery lines are completely filled with intravenous solution and no bubbles appear. After holding all delivery lines closed through valves 2, 3 and 4 so as to eliminate any leakage, the aspiration needles are inserted into the patient, following which the plunger is withdrawn or advanced rearwardly through the cylinder 120 to allow entry of intravenous solution through the port 121 into chamber 133 prior to aspiration. Here the plunger is withdrawn only partially through the chamber, for example, to the position illustrated in FIG. 8, and thereafter is fully withdrawn rearwardly though the chamber 134 to extract bone marrow from the patient while maintaining valves V₃ and V₄ open and closing valves V₁, V₂ and V₅. The mixture of bone marrow and intravenous solution is then ejected from the chamber 133 by advancing the plunger forwardly and forcing the mixture through delivery line 80 into the collection bag attached to the bag spike 107 while holding valves V₂ and V₅ open and valves V₁, V₃ and V₄ closed.

Figure 7:
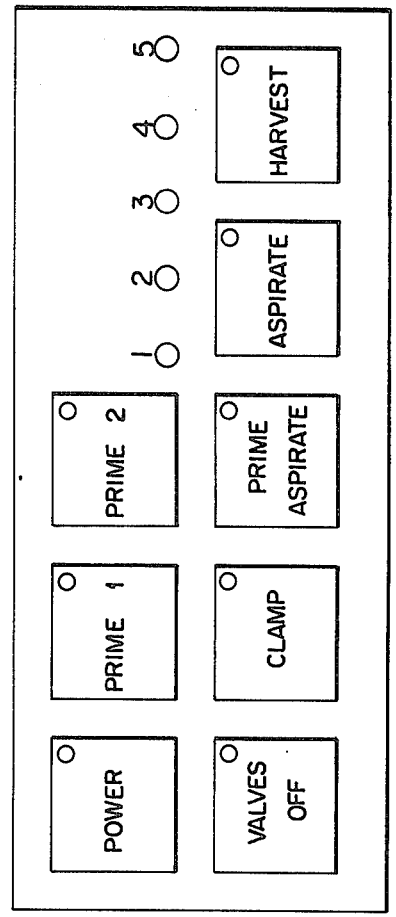
FIG. 7 is a front view of a control panel employed in regulating the operation of the apparatus.

The manner in which the valves V₁ to V₅ are controlled in opening and closing through the control panel is schematically represented in FIG. 9. As shown in FIG. 9, a suitable power source represented at 140 is connected through transformer 142 and bridge circuit 143 to a heat sink 144. In addition, the power supply is connected to the fluorescent lamp fixture 16 and through line 145 from the heat sink 144 to the valve control circuit generally designated at 150. In the valve control circuit, each of the buttons on the control panel as designated includes a manually depressable switch 152 which when depressed to a closed position serves to close the power supply into outlet lines leading to a gating circuit represented at 154 for each of the control lines into a respective valve. Each gating circuit from a control button has its output connected to a transistor 155 which in turn leads into a solenoid 156 for each respective valve. The sequence of opening and closing of the valves V₁ to V₅ is as previously described with the light displays which are designated at "1" through "5" as illustrated on the control panel in FIG. 7 being lit whenever an associated valve is closed.

It will be appreciated from the foregoing that utilization of a disposable fluid flow control assembly which can be replaceably mounted in the main cabinet greatly facilitates reuse of the apparatus in performing bone marrow transplant operations. The versatility of the system is such that while it has been described specifically for use in connection with the recovery of bone marrow for transfer to a collection bag, it may as readily used for direct delivery into a cell separator unit. Thus, in the typical cases as previously described, it is possible to remove healthy bone marrow from a cancer patient prior to chemotherapy, then to reinfuse the same bone marrow into the patient after treatment. Alternately, where bone marrow is required for patients with decreased bone marrow functions, as in aplastic anemia or other bone marrow failure, healthy bone marrow may be efficiently and relatively painlessly removed from a healthy donor and infused into the recipient patient.

It is therefore to be understood that various modifications and changes may be made in the specific sequence of steps as well as the construction and arrangement of parts in the preferred and modified forms of invention as described without departing from the spirit and scope of the present invention as defined by the appended claims.

We claim:

1. In bone marrow transplant apparatus wherein a pair of aspiration needles are insertable into the bone of a mammal in closely-spaced relation to one another, one of said aspiration needles being connectable to a bone marrow collector and the other of said aspiration needles being connectable to an intravenous solution source, the combination therewith comprising:

a first chamber interposed between said one aspiration needle and said bone marrow collector to normally establish fluid communication therebetween;

a second chamber interposed between said second aspiration needle and said intravenous solution source to normally establish fluid communication therebetween;

fluid flow control means associated with said first and second chambers to regulate the pressure level within each of said chambers such that the pressure level in said first chamber is variable between a negative pressure to induce the removal of bone marrow from the bone marrow site into said chamber and a positive pressure level operative to force the bone marrow recovered into said bone marrow collector and the pressure level in said second chamber being variable between a negative pressure level to induce the flow of intravenous solution from said intravenous solution source into said second chamber and a positive pressure level to cause said intravenous solution to flow from said second chamber through said second aspiration needle into the bone marrow site; and valve means associated with said fluid flow control means being selectively movable between open and closed positions to regulate the flow of fluid and materials to and from said first and second chambers.

2. In apparatus according to claim 1 including first delivery lines extending from fluid communication with said first chamber to said one aspiration needle and said intravenous solution source and second delivery lines extending from said second chamber to each of said bone marrow collector and said intravenous solution source.

3. In apparatus according to claim 2, said chambers and said delivery lines being in the form of a unitary disposable assembly removably positioned with respect to said fluid flow control means.

4. In apparatus according to claim 3, said valve means being associated with each of said delivery lines to regulate the flow of material therethrough.

5. In apparatus according to claim 4, each of said delivery lines being defined by a flexible conduit, said valve means each defined by a pinch valve engageable with a flexible conduit.

6. In apparatus according to claim 1, including a second solution source comprised of an intravenous solution and an anti-coagulant.

7. In apparatus according to claim 3, the concentration of anti-coagulant in said second solution source corresponding to that in said first solution source.

8. In bone marrow transplant apparatus wherein a pair of aspiration needles are insertable into the bone of a living mammal in closely spaced relation to one another, one of said aspiration needles being connectable to a bone marrow collection bag and the other of said aspiration needles being connectable to an intravenous solution source containing a mixture of intravenous solution and an anti-coagulant, the combination therewith comprising:
- a first syringe interposed between said one aspiration needle and said bone marrow collection bag to normally establish fluid communication therebetween including first delivery lines extending from fluid communication with said first syringe to said one aspiration needle and said intravenous solution source;
- a second syringe interposed between said second aspiration needle and said intravenous solution source to normally establish fluid communication therebetween including second delivery lines extending from said second syringe to each of said bone marrow collection bag and said intravenous solution source;
- fluid flow control means associated with said first and second syringes to regulate the pressure level within each of said syringes such that the pressure level in said first syringe is variable between a negative pressure to induce the removal of bone marrow from the bone marrow site into said syringe and a positive pressure level operative to force the bone marrow recovered into said bone marrow collection bag and the pressure level in said second syringe being variable between a negative pressure level to induce the flow of intravenous solution from said intravenous solution source into said second syringe and a positive pressure level to cause said intravenous solution to flow from said second syringe through said second aspiration needle into the bone marrow site; and
- valve means engageable with said first and second delivery lines being selectively movable between open and closed positions to regulate the flow of fluid and materials to and from said first and second syringes.

9. In apparatus according to claim 8, including a second solution source comprised of a mixture of an intravenous solution and anti-coagulant connectable to one of said second delivery lines.

10. In apparatus according to claim 8, said fluid flow control means including a common slide member supporting said syringes in side-by-side oppositely facing relation, said slide member having plunger-engaging members thereon, and plunger means associated with each of said syringes being simultaneously actuatable by said plunger-engaging elements to increase the pressure in one of said syringes while reducing the pressure in the other of said syringes.

11. The method of recovering bone marrow from the bone of a living mammal comprising the steps of:
- inserting first and second aspiration needles in spaced, adjacent relation to one another at the bone marrow site;
- applying a negative pressure to withdraw bone marrow and sinusoidal blood from the site through the first aspiration needle and injecting an intravenous solution under positive pressure through the second aspiration needle;
- mixing the bone marrow and sinusoidal blood in a common chamber with predetermined quantities of an anti-coagulant solution; and
- followed by delivering said mixture from said common chamber into a collection source.

12. The method according to claim 11 characterized by injecting the intravenous solution simultaneously with the withdrawal of bone marrow from the bone marrow site.

13. The method according to claim 11 including the step of mixing the bone marrow and sinusoidal blood with a mixture of an intravenous solution and an anti-coagulant.

* * * * *